United States Patent [19]

Whittle

[11] Patent Number: 5,466,452
[45] Date of Patent: Nov. 14, 1995

[54] PHARMACEUTICAL COMPOSITIONS FOR THE TREATMENT OF SKIN DISORDERS

[75] Inventor: Brian A. Whittle, Hornsea, United Kingdom

[73] Assignee: Phytopharm Ltd., North Humberside, United Kingdom

[21] Appl. No.: 108,640

[22] PCT Filed: Feb. 28, 1992

[86] PCT No.: PCT/GB92/00359

§ 371 Date: Aug. 26, 1993

§ 102(e) Date: Aug. 26, 1993

[87] PCT Pub. No.: WO/9215314

PCT Pub. Date: Sep. 17, 1992

[30] Foreign Application Priority Data

Feb. 28, 1991 [GB] United Kingdom ............... 9104286

[51] Int. Cl.⁶ ............................................. A61K 35/78
[52] U.S. Cl. .................. 424/195.1; 514/783; 514/858; 514/859; 514/860; 514/861; 514/862; 514/863; 514/864; 514/865
[58] Field of Search ............... 424/195.1; 514/858–865

[56] References Cited

U.S. PATENT DOCUMENTS

| | | | |
|---|---|---|---|
| 3,993,756 | 11/1976 | Kaneda et al. | 424/195.1 |
| 4,247,636 | 1/1981 | Schoenrock et al. | 435/94 |
| 4,627,934 | 12/1986 | Lindauer et al. | 252/522 R |
| 4,804,545 | 2/1989 | Goering et al. | 426/28 |
| 4,906,470 | 3/1990 | Liu | 424/195.1 |
| 4,937,073 | 6/1990 | Fujikara et al. | 424/195.1 |
| 5,013,561 | 5/1991 | Goering et al. | 426/28 |

FOREIGN PATENT DOCUMENTS

| | | |
|---|---|---|
| 56-092216 | 7/1981 | Japan. |
| 60-181022 | 9/1985 | Japan. |
| 613562 | 11/1948 | United Kingdom. |
| WO87/06833 | 11/1987 | WIPO ............... A61K 33/24 |

OTHER PUBLICATIONS

Sasaki et al. *Chem. Pharm. Bull.* vol. 30 pp. 3555–3562, (1982), [Abstract Only].

Sasaki et al. *Chem. Pharm. Bull.* vol. 29(6), pp. 1636–1643, (1981), [Abstract Only].

Xu et al. *Yao Hsueh Hsueh Pao*, vol. 14, pp. 461–466 (1979), [Abstract Only].

Kong et al. *Amer. J. Chin. Med.*, vol. 4, pp. 105–128, (1976), [Abstract Only].

*Primary Examiner*—Douglas W. Robinson
*Assistant Examiner*—Howard C. Lee
*Attorney, Agent, or Firm*—Bacon & Thomas

[57] ABSTRACT

A process is provided which is suitable for the preparation of herbal compositions for the treatment of skin disorders such as eczema and psoriasis. The process comprises preparing an extract or extracts of herbs which provide an anti-inflammatory agent, an adrenocortical stimulant and a cortisol protecting agent by steam distillation and decoction and then treating the extracts to reduce the polysaccharide and/or sugar content. This is achieved by fermentation or enzymic action or by extraction with a solvent having a polarity in the range E° 0.4 to 0.95 or by precipitation with an inorganic compound and/or colloid or by a combination of two or more of the above. As a final concentration step, the material is further purified by extraction with a solvent having a polarity in the range mentioned above. The reduction of the sugar/polysaccharide content greatly improves the handling characteristics of the extract which can be dried to a free flowing powder. Tablets and capsules for oral administration can be prepared from the extract and it is also suitable for the preparation of topical compositions.

24 Claims, No Drawings

PHARMACEUTICAL COMPOSITIONS FOR THE TREATMENT OF SKIN DISORDERS

The present invention relates to extracts of herbal compositions for use in the treatment of skin disorders such as, for example eczema and psoriasis and to processes for their preparation.

The etiology of eczema and psoriasis is not completely understood. However the symptomotology which characterizes the conditions is well described. The most important features are:

inflammation and pruritus (itching) which leads to a cycle of further irritation, inflammation and itching.

Eczema and psoriasis are expressions of an inappropriate immunological response whereby the body reacts to some of its tissue components as though they were foreign. Treatment is directed towards diminishing the severity of the immune response and alleviating symptoms. In conventional Western medicine topical corticosteroids are used to reduce inflammation and to suppress the immune response. Emollients are used to physically protect and smooth the skin and, where the skin is infected, antiobiotics are used.

Practitioners in traditional Chinese medicine however use decoctions of herbs for oral and topical treatment of dermatological conditions including eczema and psoriasis. A wide variety of agents have been used and in traditional Chinese medicine it is conventional to use a compound prescription which is designed by the practitioner after careful examination of the individual patient. It has been found by clinical experimentation that mixtures of certain herbs can be used to provide a composition which is effective in a large proportion of patients suffering from eczema and psoriasis, without recourse to individualisation of treatment. Different formulae have been devised for dry, weeping, infected and lichenified eczema although the mode of action of traditional Chinese medicines is not fully understood.

Table I shows a number of Chinese herbs which are traditionally used for the treatment of skin disorders together with the principle constituents and their pharmacological actions (Chang and But; Pharmacology and Applications of Chinese Materia Media. World Scientific Publishing 1986, Volumes I and II). The table shows that many of the agents traditionally used have pharmacological properties which are appropriate for the treatment of symptoms of eczema and psoriasis, namely anti-inflammatory, analgesic, anti-pyretic, anti-pruritic, anti-bacterial and immune suppressent activity. Some of the agents listed may stimulate the adrenal cortex to produce endogenous corticosteroids and others may inhibit the breakdown of cortisol in certain tissues such as the skin and lung. The combination of herbs to provide a combined attack on the symptoms of eczema and psoriasis are therefore rational even though at present it is not known exactly which of the constituents are responsible for the beneficial therapeutic effects of the mixtures.

It is possible that some of the herbs in the mixtures are necessary in order to increase the solubility of some of the active constituents in water since the traditional method of preparing extracts is by decoction i.e. boiling in water. In traditional Chinese medicine some herbs are included in prescriptions because they act as demulcents i.e. agents which have a soothing effect on the gastrointestinal tract and facilitate patient acceptance. It is firmly believed by traditional Chinese practitioners that the toxicity of mixtures of herbs is less than that of the herbs given in isolation. Although this has yet to be rigorously proved in controlled clinical trials, conventional wisdom indicates that some of the herbal components have biological activities which summate, and others antagonise the toxic effect of active components. Until the active components have been identified with certainty it has proved prudent to use a decoction, extract or fractionated extract of a plurality of herbs. To be useful in practice it is necessary to have one or more fixed composition mixtures. Surprisingly, it has been found that fixed combinations of specific herbs can be used to treat different types of eczema and psoriasis.

For example a particularly useful formulation of 10 herbs which has been found to be effective in the treatment of dry ("red all over") childhood eczema can be prepared by adding about 300 ml of water to every 38.75 g of herb contained in a (non-aluminium) saucepan, bringing to the boil and simmering for one and a half hours. During this process the volume of liquid is reduced until a volume of about 50 ml per 38.75 g of original herb is obtained. The final volume of the decoction is not critical and when removed from the exhausted herbs can be diluted to taste. The decoction obtained from the herbs is prepared fresh each day. Some of the herbs contain volatile oil and these herbs are added three minutes before the end of the decoction period to minimise loss of volatile oil.

The process of decoction is efficient in the extraction of the active principals but additionally a large quantity of inactive material in the form of polysaccharides, colouring matter, sugars and tannins is also extracted. There is therefore a need for a method of preparing herbal extracts which are more concentrated in respect of the active ingredients and contain much lower amounts of extraneous material than those extracts hitherto known.

The present inventors have devised a method by which this might be achieved which allows a smaller dosage unit to be administered.

Thus a process for the preparation of a composition for treating skin disorders in accordance with the invention comprises:

(a) preparing an extract or extracts of a plurality of herbs, the herbs being such as to provide an anti-inflammatory agent, an adrenocortical stimulant and a cortisol-protecting agent by subjecting said herbs to steam distillation and decoction, (b) reducing the amount of polysaccharides and/or sugars in at least a proportion of the extract or extracts to less than 5% by weight under conditions which do not substantially reduce the content of glycosides which are present in said material by one or more of:
  (i) fermentation or enzymatic action,
  (ii) extraction with a solvent having a polarity in the range $E^o$ 0.4 to 0.99 or a mixture of solvents at least one of which has a polarity in said range,
  (iii) precipitation with an inorganic compound and/or a colloid, and (c) concentrating the active agents present in the extracted material by further extraction with a solvent having a polarity in the range $E^o$ 0.4 to 0.99 or a mixture of solvents at least one of which has a polarity in said range.

The preparation of an extract in step (a) of the above method is advantageously carried out by the traditional decoction process of boiling the herbs in water. Prior to decoction any volatile oils or other volatile components can be removed from the herbs by steam distillation and retained for re-introduction into the final extract if desired. These volatile components can be particularly useful in the formulation of treatments for eczema and psoriasis.

The reduction of the polysaccharides and/or sugar carried out in step (b) is extremely important in the process of the invention. Extracts containing substantial amounts of sugars are very difficult to evaporate to a free flowing powder and often nothing more than a solid sticky mass can be achieved. Preferably the amount of polysaccharides and/or sugars is reduced to less than 2.5% and more preferably less than 5% by weight. It is also important that the step for reducing excess polysaccharides and sugars is carried out under conditions which do not substantially reduce the glycoside content since one or more of the active agents may be a glycoside.

Where the polysaccharide and/or sugar content is to be reduced by fermentation it is preferable to incubate the total water extraction from the decoction prepared in step (a) with barley malt or with a yeast such as saccharomyces cerevisiae or a fungus such as *Aspergillus oryzae* or other microorganism providing amylase and/or saccharolytic enzymes. Isolated and purified amylolytic or saccharomytic enzymes may also be used, optionally bound to a membrane or other support. Where these enzymes will also split glycosides it is preferable to use an inhibitor of glycosidase.

In a fermentation process ethyl alcohol may be formed in situ and may be used in a further separation of active ingredients.

If the polysaccharide and/or sugar content is to be reduced by the further extraction of the initial extract with a solvent or mixture of solvents at least one of which has a polarity in the range $E^o$ 0.4 to 0.99 it is preferable if the solvent is one or more of chloroform, methylene chloride, ethyl acetate, tetrahydrofuran, methylethylketone, acetone, acetonitrile, propanol, ethanol, methanol, industrial methylated spirits or a not less than 70% solution of one or more of the above in water. Particularly preferred are 70% solutions of ethanol, propanol or industrial methylated spirits.

The addition of these solvents results in a fractional precipitation of polysaccharide and/or sugars, the desired active components remaining in solution.

As an alternative to, or as well as fermentation, enzymic treatment and/or solvent extraction in step (b) the polysaccharide and/or sugar content can be reduced by precipitation with an inorganic compound and/or a colloid. A preferable inorganic compound for use is calcium hydroxide.

After the sugar reducing step a further concentration of the extract is generally required. In particular it is desirable to substantially rid the extract of polyphenyls and tannins. In the process of the invention this is achieved by the further extraction step (c) using a solvent or mixture of solvents at least one of which has a polarity in the range $E^o$ 0.4 to 0.99. Suitable solvents may be selected from the list given above in connection with step b(ii).

The extract produced by the process of the invention may be evaporated to a paste, mixed with excipients and extruded to granules for oral administration, optionally with the addition of flavourings.

The extract prepared may be diluted in an aqueous solution for oral administration. The invention particularly provides compositions containing the herbal extract made by the process of the invention containing an anti-inflammatory agent, an adrenocorticol stimulant and a cortisol protecting agent which is admixed with a pharmaceutically suitable excipient, diluent or carrier many examples of which are well known to the man skilled in the art. A particularly useful carrier is silica gel.

For example the composition may be prepared for topical administration using well established formulations which produce an emollient ointment or water dispensable cream. The composition may also be prepared in a unit dosage form such as a tablet or capsule for oral administration. For such use it is advantageous if after the final extraction step the herbal extract is processed to form a powder, for example by spray drying, freeze drying or evaporation.

Chinese medicine teaches that substantially all of the herbs in a composition are necessary for activity and that the herbs are best given in extemporaneously prepared decoction. However it has now surprisingly been found that the anti-eczema activity of the composite herbal preparation resides mainly, if not exclusively in a restricted number of herbs. It is therefore possible to reduce the amount of unnecessary material from the composition by limiting the number of herbs used, and to then further reduce the quantity of material given by preparing a composition in concentrated form in accordance with the invention wherein extraneous materials are removed.

Herbs selected from the list in Table I are suitable for use in the invention and a particularly preferred composition is one containing extracts from *Rehmannia glutinosa, Dictamnus augustifolia, Glycyrrhiza uralensis* and either *Ledebouriella sesloides* or *Schizonepeta tenuifolia*. Optionally Tribulus terrestris can be included. Another preferred composition is one containing the first 10 herbs listed in Table I.

It is preferable if one of the herbs included in the mixture provides an anti-pruritic (anti-itching) agent. As some of the herbs may have a bitter taste it is also preferable to add a sweetening agent for oral compositions.

The herbal extract may be prepared in accordance with the invention either by carrying out steps (a), (b) and (c) on a plurality of herbs which are first mixed together or by carrying out steps (a), (b), (c) on some or all of the individual herbs and mixing together the final extracts.

A disadvantage of the former method is that the yield of active ingredient from each herb varies from batch to batch so that the final concentration of each active agent in the mixture will not be known. By preparing separate extracts of each herb and then later mixing them, each may be assayed using a marker substance which assists in standardizing the dose given to the patient. A further advantage is that full processing for sugar reduction need only be carried out on those herbs in the mixture having a high polysaccharide or sugar/content which makes them difficult to handle.

The invention is now illustrated in the following non-limiting examples.

Example 1

The following ingredients are coarsely chopped or powdered and volatile oil is removed by steam distillation:

|  | Weight in Grams |
| --- | --- |
| *Radix Ledebouriellae* | 112.5 |
| *Fructus Tribuli* | 112.5 |
| *Caulis Akebiae* | 112.5 |
| *Radix Rehmanniae* (raw) | 168.75 |
| *Radix Glycyrrhizae* | 56.25 |
| *Radix Paeonia* rub. | 112.5 |
| *Cortex Dictamni* | 168.75 |
| *Moutan radicis* | 112.5 |
| *Gypsum Fibrosum* | 450.0 |
| *Artemisia scopariae* | 112.5 |

The oil is reserved and the residue is mixed with one litre of water, boiled for one and a half hours and allowed to cool to a temperature of 35° C. to form a decoction.

100 ml of an actively growing culture of fresh baker yeast is added to the mixture of herbs and water and maintained with stirring for 8 hours or until the sugar content of an aliquot is less than 0.4%.

The vegetable matter is removed by straining and yeast is removed from the liquor by centrifugation. The filtered liquid is evaporated to dryness.

The extract thus prepared is stirred with 200 ml of ethyl acetate for 10 minutes, separated by centrifugation and the solution reserved. A further quantity of 50 ml ethyl acetate is added, the mixture, stirred and separated. The combined filtrate is evaporated to dryness.

The reserved oil is added back. The resulting product is a brown extract which is free flowing and can be used, with suitable flavourings, as the dosage form. It can be formulated into conventional pharmaceutical dosage forms, with addition of excipients, for the treatment of dry eczema. The quality given above is sufficient for 10 days treatment of an adult.

Example 2

The following herbs are coarsely chopped or powdered and decocted with 4 litres of water for 1 hour:

|  | Weight in Grams |
| --- | --- |
| Radix Rehmanniae (raw) | 168.75 |
| Radix Paeonia rubra | 112.50 |
| Radix Glycyrrhizae | 56.25 |
| Cortex Dictamni radicis | 168.75 |
| Rhizoma Smilacis glabrae | 168.75 |
| Fructus Kochiae | 56.25 |
| Radix Angelica sinensis | 112.50 |
| Semen Sesami (black) | 168.75 |

The liquor is removed by centrifugation. The extract is then evaporated until it contains 50% solids w/v and 10% by weight calcium hydroxide is added. Three volumes of isopropanol are added with mixing and the mixture allowed to stand at room temperature. The clear supernatant is removed, 1 volume of 75% isopropanol added, mixed and the residue centrifuged. The pooled supernatants are evaporated to dryness. The resulting refined extract can be mixed with pharmaceutical aids and filled into capsules or compressed into tablets.

Example 3

An extract containing the following herbs is prepared:

|  | Weight in Grams |
| --- | --- |
| Ledebouriella sesloides | 10 |
| Paeonia rubra | 12 |
| Rehmannia glutinosa | 10 |
| Glycyrrhiza uralenis | 15 |

For the herbs *Ledebouriella sesloides* and *Paeoniae rubra* a decoction is prepared of each of the herbs individually by boiling in successive quantities of water until complete exhaustion of the marc. The extracts are dried.

Extracts of each of the herbs *Rehmannia glutinosa* and *Glycyrrhiza uralenis* are prepared by the method of Example 2. The dried extracts of all four herbs are combined in the weights shown above which provides an adult daily dose for the treatment of eczema.

Example 4

An extract is prepared from a mixture of the following herbs using the method described in Example 2:

|  | Weight in Grams |
| --- | --- |
| Radix Rehmanniae (raw) | 90 |
| Rhizoma Smilacis glabrae | 90 |
| Radix Glycyrrhizae | 30 |
| Cortex Dictamni Radicis | 90 |
| Radix Paeonia Rub | 60 |
| Radix Artemisia scopariae | 60 |
| Fructus Kochiae | 30 |
| Sophora flavescens | 20 |
| Rhizoma atractyloides | 60 |

The composition is suitable for treatment of chronic, lichenified, "weeping" eczema, and the quanities given are suitable for 10 days treatment of an adult patient.

Example 5

An extract is prepared from a mixture of the following herbs using the method described in Example 2:

|  | Weight in Grams |
| --- | --- |
| Rhizoma Similacis glabrae | 300 |
| Cortex Dictamni Radicis | 100 |
| Radix Clematidis | 100 |
| Radix Angelica sinensis | 100 |
| Radix Polygonum multiflora | 100 |
| Radix Salvia miltiorrhiza | 100 |
| Rhizoma Ligustiae chuanxiong | 100 |

The composition is suitable for treatment of "stable" psoriasis and the quanitites given are suitable for 10 days treatment of an adult patient.

Example 6

An extract is prepared from a mixture of the following herbs using the method described in Example 2:

|  | Weight in Grams |
| --- | --- |
| Rhizoma Smilacis glabrae | 300 |
| Cortex Dictamni Radicis | 100 |
| Radix Clematidis | 100 |
| Radix Rhemanniae | 200 |
| Rhizona Imperata cylindrica | 100 |
| Radix Arnebiae (Ser) lithospermum | 10 |
| Radix Salvia miltiorrhiza | 10 |
| Radix Ligustiae chuanxiong | 10 |
| Carthamus tinctorus | 10 |

The composition is suitable for the treatment of progressive psoriasis and the quantities given above are suitable for 10 days treatment of an adult patient.

Example 7

A refined extract is prepared according to the method given in Example 2 from the following herbs and then mixed with an emulsifying ointment base to produce an oil/water cream:

*Phellodendron anurense* (extract from 20 g herb)

*Scutellaria baicalensis* (extract from 20 g herb)
*Coptis chinensis* (extract from 20 g herb)
Cetomacrogol Emulsifying Ointment to 100 g Example 8

A refined extract is prepared according to the method given in Example 2 from *Sophora flavescens*, and incorporated in an emulsifying ointment base according to the following formula:

| | |
|---|---|
| *Sophora flavescens* | (extract from 20 g herb) |
| Emulsifying wax | 30 g |
| Hard paraffin | 5 g |
| Cod liver oil | 15 g |
| Evening Primrose Oil | 15 g |
| White Soft Paraffin to | 100 g |

This ointment can be applied thinly to the skin or can be mixed with water to produce an oil in water emollient cream.

Example 9

A refined extract prepared according to the method given in Example 2 from *Rheum palmatum* is incorporated in an emulsifying ointment base:

*Rheum Palmatum* (extract from 30 g herb)
Cetomacrogol Emulsifying Ointment to 100 g In this example and in Examples 7 and 8 the quantity of extract of herb is illustrative and not limited to the proportions given.

Example 10

A decoction was prepared using the method given in Example 1 from 38.75 g of the herbs listed in that Example to give a final volume of 50 ml. Using a proprietary test kit, approximate dilutions of the decoction were tested for sugar before, and at intervals after adding 3 ml of a fresh 10% yeast suspension to the decoction. The mixture was incubated at 30° C. with occasional stirring.

| Time (h) | Approx concentration of sugar as tested | Dilution | Concentration in decoction by weight |
|---|---|---|---|
| 0 | >0.2% | 1:300 | >30% |
| ½ | 0.2–0.4% | 1:50 | 10–20% |
| 1 | 0.2–0.4% | 1:10 | 2–4 |
| 2 | 0.2–0.4% | 1:1 | 0.2–0.4% |

*Limit of detection of glucose oxidase test kit.

After fermentation, the decoction is markedly less sweet although there is residual sweetness contributed by the liquorice contained in the mixture. When the resulting solution is filtered and evaporated to dryness 4.7 g of extract is produced. Example 11

The following herbs are coarsely chopped and volatile oil is removed by steam distillation:

| | Weight in Grams |
|---|---|
| Radix ledebouriellae | 300 |
| Fructus Tribuli | 300 |
| Lacca | 450 |
| Caulis Akebiae | 300 |
| Radix glycyrrhizae | 150 |
| Radix Rehmanniae (raw) | 450 |
| Radix Paeonia rubra | 300 |
| Herba Lophatheri | 300 |
| Cortex Dictamni radicis | 450 |
| Herba Schizonepetae | 150 |
| | 3100 g |

The oil is reserved and the residue is mixed with one litre of water, boiled for one and a half hours and allowed to cool to a temperature of 35° C. to form a decoction.

100 ml of an actively growing culture of fresh bakers yeast is added to the mixture of herbs and water and maintained with stirring for 8 hours or until the sugar content of an aliquot is less than 0.4%.

The vegetable matter is removed by straining and yeast is removed from the liquor by centrifugation. The filtered liquid is evaporated to dryness.

The extract thus prepared is stirred with 200 ml of 70% industrial methylated spirits for 10 minutes, separated by centrifugation and the solution reserved. A further quantity of 50 ml 70% industrial methylated spirits is added, the mixture stirred and separated. The combined filtrate is evaporated to a syrupy consistency. Weight per ml is determined and ⅓ of this weight of colloidal silica added, and the extract evaporated to dryness.

The resulting dry extract is a brown extract which is free flowing and can be used, with suitable flavourings, as the dosage form as powder, granules, capsules or tablets, for the treatment of dry eczema. These quantities are sufficient for 20 days treatment for an adult.

TABLE I

| CHINESE PLANT NAME | LATIN NAME | CONSTITUENTS | PHARMACOLOGY | TRADITIONAL USE IN CHINA |
|---|---|---|---|---|
| Bai Tai Weng | *Potentilla chinensis* | triterpenoid seponins | Antibacterial, anti-trichomonal, anti-amoebic | Bacillary dysentery, amoebic dysentery, lymph node TB, Squamous cell cancer |
| Dihuang | *Rehmannia glutinosa* (Libosch) (Scrophulatiaceae) | β-sitosterol, mannitol, stigmasterol, campesterol, catalpol, rehmannin, vitamin A | Reduction of cortisol, diuretic, anti-inflammatory, anti-fungal | Immunological diseases, infectious hepatitis, hypertension, neurodermatitis |
| Chi Shao | *Radix paeoniae* | paeoniflorin, | Vasodilator. Increases | Pain in chest, pain in |

TABLE I-continued

| CHINESE PLANT NAME | LATIN NAME | CONSTITUENTS | PHARMACOLOGY | TRADITIONAL USE IN CHINA |
|---|---|---|---|---|
| | lactiflorae/veitchii (Ranunculaceae) | albiflorin, oxypaeoniflorin, benzoylpaeoniflorin, benzoic acid, tannin | coronary blood flow, increases myocardial oxygen, inhibits platelet aggregation, sedative, analgesic, antispasmodic, anti-inflammatory | abdomen, dysmenorrhoea, amenorrhoea, carbuncle, epistaxis, conjunctival congestion, traumatic injury |
| Bai Xan Pi | Dictamnus augustifolia Chinese Dittany Root bark + (Rutaceae) | Dictamnine, dictamnolactone, sitosterol, obacunic acid, trigonelline, choline campesterol, fraxinellon shimmianine fagarine, dasycarpamine | Cardiotonic, antifungal, smooth muscle stimulant, antipyretic, shortened clotting time (iv) | Anti-rheumatic, anti-inflammatory, pityriasi8 rosea, scabies, dermatomycoses, prurigo, rheumatic pain, jaundice |
| Gan Cao | Glycyrrhiza uralensis (Fisch) Licorice (Leguminosae) | Triterpenes (glycyrrhizin 'G' etc) Flavonoids (liquiritin etc) Berniarin, umbelliferone, ferulic acid, sinapic acid etc. | Adrenocorticomimetic, anti-inflammatory, anti-ulcer, antispasmodic, detoxicant | Addisons Disease, gastric & duodenal ulcer, pulmonary TB, infectious hepatitis, eye inflammatory disease, purpina |
| Fang Feng | Ledebouriella sesloides | Volatile oil, mannitol, bitter glycosides, phenolic glycosides, polysaccharides, organic acids | Anti-inflammatory, analgesic, antipyretic, anti-convulsant, antimicrobial | Rosacea, common cold, elimination of heavy metals, pnnitus, urticaria |
| Ci Ji Li (Bai Ji Li) | Tribulus terrestria/Fructus tribuli | Diosgenin, ruscogenin, hecogenin, tribuloside, kaempferol, rutoside, astragalin, harmine | Hypotensive effect on smooth muscle, diuretic, cough suppressant | Headache, dizziness, red eye, itching, chest |
| Dan Zhu Ye | Lopatheri gracile | Arundoin, cylindrin, friedelin, taraxerol, β-sitosterol | Antibacterial, diuretic, antipyretic | Febrile disease, stomatitis swelling & pain in gingivae, urethral inflammation and pain |
| Jing Jie Sui | Schizonepeta tenuifolia | d-menthone, l-pulegone, schizoneptosides A & B d-limone | Antipyretic, antibacterial, anti-inflammatory, analgesic, aniitubercular | Influenza fever, headache, sore throat, measles, urticaria |
| Mu Tong | Akebia trifoliata | Akebin which hydrolyses to hederagenic, oleandic acid, rhamnose & glucose | Diuretic, cardiotonic, stimulation of GI tract smooth muscle, uterine SM relaxant, antifungal | Urinary infections, oedemia, amenorrhoea, diarrhoea, period pain, prelapse uterus |
| Lei Gong Teng | Trypterigium wilfordii | Wilfordine, and related alkaloids, celacemine and other macrocyclic alkaloids, triptolide and other epoxyditerpenes, celastol and other triterpenes | Anti-inflammatory, antineoplastic, immunosuppressant, insecticide | Anthelmintic, anti-inflammatory, anti-rheumatic |
| Ku Shen | Sophora flavescens | Matrine, oxymatrine, sophoranol, flavonoids, cytosine | Diuretic, antineoplastic, immunosuppressant, bradycardia, reduced myocardial contractility, hypotensive, bronchodilator, antimicrobial | Anthelmintic, anti-inflammatory, jaundice, scabies, enteritis, dysentery |
| Bei Yin Chen | Artemesia scopariae | Volatile oil, cholorogenic acid, caffeic acid, capillarisin, methylcapillarisin, phenoxychromones, flavonoids | Antipyretic, cholagogue, hepatoprotective, antilipidaemic, hypotensive, antibacterial | Jaundice, hepatitis |
| Mu Dan Pi (Moutan) | Paeonia suffructicosa | Paeonol, paeonoside, paeonolide, paeoniflorin, volatile oil, phytosterol | Antimicrobial, anti-inflammatory, hypotensive analgesic | Convulsions, ulcers, fractures, concussion, sprains |
| Zhi Mu | Anemarrhena asphodeloids | Saponins, sarsasapogenin, | Adrenocortical stimulation, | Dry cough, fever |

TABLE I-continued

| CHINESE PLANT NAME | LATIN NAME | CONSTITUENTS | PHARMACOLOGY | TRADITIONAL USE IN CHINA |
|---|---|---|---|---|
| | | markogenin, neogitogenin, chimonin, isomangiferin | hypoglycaemic, antibacterial | |
| Dang Gui | Angelica sinensis | Volatile oil, ligustilide, butylidenephthalide, butanedioic acid, angelicane, β-sitosterol, vitamins $B_{12}$, A & E, nicotinic acid, folic acid, ferulic acid, succinic acid | Immunosuppressant, anti-inflammatory, uterine relaxant, hypotensive, anti-platelet aggregation, antilipidaemic | Dysmenorrhea, anaemic, amenorrhoea, headache, constipation, rheumatism |
| Zi Cao | Lithospermum erythrorhizon | Acetylshikonin, β-, dimethylactylalkannin skikonin | Antineoplastic, antipyretic | Fever, eczema |
| Di Fu Zi | Kochia scopariae | Kochiasides | Anti-inflammatory | Eczema, pruritus, rheumatism |
| Tu Fu Ling | Smilacis Glabrae | Sarsagogenin, triterpene, glycosides | Immunosuppressant, anti-inflammatory | Eczema, leukorrhea, lymphedema, muscle cramp |
| Chuan Xiong | Rh. Ligusticum chuanxiong | Volatile oil, alkaloids, phenolic compounds, Lactones | β-agonist, coronary dilator, peripheral dilator, vasodilators, inhibition of platelet aggregation | Analgesic, rheumatism, sores, ulcers, dysmenorrhoea |
| Dan Shen | Salvia miltiorrhiza | Tanshinones I, IIa, IIb, miltirone, isotanshinones, salviol etc. | Improvement of circulation | Angina, pectoris, amenorrhoea, dysmenorrhoea, fractures, sprains, insomnia |
| He Shou Wu | Polygonum multiform | Anthraquinone, glycosides & aglycones | β-blocker, lipid-lowering, antibacterial | Tinnitus, weakness of lower back, constipation |
| Bai Mao Gen | Imperata cylindrica | Cyclindrin, arunoin, ferneol | Diuretic, coagulant | Urinary tract infection, oedema, jaundice |
| Hong Hua | Carthamus tinctorius | Dihydroflavone, glycosides | Cardiotonic | Amenorrhoea, dysmenorrhoea, fractures, concussion, sprains |
| Cang Zhu | Atratylodes chinensis | β-eudesmol, hinesol, atractylodin | Antiseptic. Hypoglycaemic, diuretic, gastritis, antispasmodic | Rheumatism, oedema, diarrhoea, abdominal distention |
| Wei Ling Xian | Clematis chinensis | protoanemonin, anemonol, sterols, saponins | Antihistaminic, antibacterial, induction of labour, vasodilator | Rheumatism, arthritis, numbness of limbs, traumatic injury, psoriasis |
| Huang Bo | Phellandendron amurense | berberine, phellandendrine, magnoflorine, palmatine, obakulactone, obakunone | Anti-micobial Hypotensive muscle relaxant | Decongestant |
| Huang Qin | Scutellaria baicalensis | β-sitosterol, benzoic acid, baicalein, baicalin, wogonin, wogonoside | Anti-microbial, sedative, antipyretic, hypotensive, anti-inflammatory, diuretic, anti-cholinergic | Fever, cough, pneumonia, jaundice, hepatitis, dysentery. conjunctivitis, hypertension |
| Huang Lian | Coptis chinensis | berberine, coptisine, worenine and other alkaloids | Antimicrobial, anti-cholinergic, hypotensive, muscle relaxant | Nausea, vomiting, dysentery, enteritis, conjunctivitis, otitis media |
| Da Huang | Rheum palmatum | anthraquinones, glycosides, sennosides tannins | Cathartic action, antispasmodic, choloretic action | Indigestion, jaundice, amenorrhoea, burns and scalds |

Glossary of Terms

The terms used define the identity of the plant or ingredient are given in the examples as Latin binomial names. The parts of the plant used are defined as follows:

| | |
|---|---|
| Caulis - | Stem |
| Cortex - | Bark |
| Cortex radicis - | Root Bark |
| Herba - | Aerial parts |
| Fructus - | Fruit |

| | |
|---|---|
| Radix - | Root |
| Rhizoma - | Rhizome |
| Semen - | Seed |
| Spika - | Flowering spike |

I claim:

1. A process to make a composition for treating eczema, psoriasis, pruritis and inflammatory reactions of the skin which comprises:
   (a) subjecting a plurality of herbs having anti-inflammatory activity, adrenocortical stimulating activity and corticosol-protecting activity to steam distillation and decoction, to produce an extract of the herbs;
   (b) reducing the amount of polysaccharides and/or sugars, in the extract to less than 5% by weight under conditions which do not substantially reduce the content of glycosides which are present in said material by one or more of:
      (i) fermenting with barley malt or with a microorganism which produces amylase and/or saccharolytic enzymes or by using isolated amyolytic or saccharolytic enzymes,
      (ii) extracting with a solvent having a polarity in the range E° 0.4 to 0.99, or a mixture of solvents at least one of which has a polarity within said range,
      (iii) precipitating the polysaccharide and/or sugar with an inorganic compound; and
   (c) concentrating the active agents present in the extracted material by further extracting with a solvent having a polarity in the range E° 0.4 to 0.99, or a mixture of solvents, at least one of which has a polarity within said range,
wherein the herbs are selected from the group consisting of *Potentilla chinensis* (Bai Tai Weng), *Rehmannia glutinosa* (Dihuang), *Radix paeoniae lactiflorae/veitchii* (Chi Shao), *Dictamnus augustifolia* (Bai Xan Pi), *Glycyrrhiza uralensis* (Gan Cao), *Ledbouriella sesloides* (Fang Feng), *Tribulus terrestris* (Ci Ji Li), *Lopatheri gracile* (Dan Zhu Ye), *Schizonepeta tenuifolia* (Jing Jie Sui), and *Akebia trifoliata* (Mu Tong).

2. A process as claimed in claim 1 wherein the microorganism used in step b(i) is *Saccharomyces cerevisiae* or *Aspergillus oryzae*.

3. A process as claimed in claim 1 wherein the isolated amylolytic or saccharolytic enzymes used in step b(i) are used in the presence of an inhibitor of glycosidase.

4. A process as claimed in claim 1 wherein the isolated amylolytic or saccharolytic enzymes used in step b(i) are bound to a support.

5. A process as claimed in claim 4 wherein the support is a membrane.

6. A process as claimed in claim 1 wherein, when the polysaccharide content or sugar content, or both, is reduced by the solvent extraction of the active agents in the method of step b(ii), the solvent is selected from the group consisting of chloroform, methylene chloride, ethyl acetate, tetrahydrofuran, methylethylketone, acetone, acetonitrile, propanol, ethanol, methanol and industrial methylated spirits.

7. A process as claimed in claim 1 wherein, when the polysaccharide content and/or sugar content is reduced by the solvent extraction of the active agent in the method of step b(ii) the solvent used is a 70% or greater solution in water of a solvent selected from the group consisting of chloroform, methylene chloride, ethyl acetate, tetrahydrofuran, methylethylketone, acetone, acetonitrile, propanol, ethanol, methanol and industrial methylated spirits.

8. A process as claimed in claim 1 wherein, when the polysaccharide content and/or sugar content is reduced by the precipitation method of step b(iii), the inorganic compound is a colloid.

9. A process as claimed in claim 1 wherein when the polysaccharide content and/or sugar content is reduced by the precipitation method of step b(iii), the inorganic compound is calcium hydroxide.

10. A process as claimed in claim 1 wherein in the solvent extraction method of step (c), the solvent is selected from the group consisting of chloroform, methylene chloride, ethyl acetate, tetrahydrofuran, methylethylketone, acetone, acetonitrile, propanol, ethanol, methanol and industrial methylated spirits.

11. A process as claimed in claim 1 wherein in the solvent extraction method of step (c), the solvent used is a 70% or greater solution in water of a solvent selected from the group consisting of chloroform, methylene chloride, ethyl acetate, tetrahydrofuran, methylketone, acetone, acetonitrile, propanol, ethanol, methanol and industrial methylated spirits.

12. A process as claimed in claim 10 wherein tannins and polyphenyls are removed from the extracted material.

13. A process as claimed in claim 1 wherein volatile oils and other volatile components which are removed during steam distillation are retained and reintroduced into the composition.

14. A process as claimed in claim 1 which further comprises drying the concentrated extract to powder form.

15. A process as claimed in claim 14 wherein drying is effected by evaporating, spray drying or freeze drying.

16. A process as claimed in claim 1 wherein the herbal extract from step (c) is dried to a paste, mixed with excipients and extruded to form granules.

17. A herbal extract for treating skin disease comprising an anti-inflammatory agent, an adrenocortical stimulant and a cortisol-protecting agent when produced by a process as claimed in claim 1.

18. An extract as claimed in claim 17 when admixed with a pharmaceutical excipient, diluent or carrier.

19. An extract as claimed in claim 18 wherein the carrier is silica gel.

20. An extract as claimed in claim 17 which is prepared in unit dosage form.

21. An extract as claimed in claim 17 which is in the form of an aqueous solution.

22. An extract as claimed in claim 17 which is in the form of an ointment or cream.

23. A process as claimed in claim 1 wherein the composition comprises:
   (a) *Rehmannia glutinosa* as a cortisol-protecting agent and adrenocortical stimulant;
   (b) *Dictamnus augustifolia* as an alkaloid component,
   (c) *Glycyrrhiza uralensis* as an adrenocortical stimulant, and
   (d) *Ledbouriella sesloides* or *Schizonepeta tenuifolia* as an anti-inflammatory agent.

24. A process as claimed in claim 23 wherein the composition further comprise *Tribulus terrestris*.

* * * * *

UNITED STATES PATENT AND TRADEMARK OFFICE
CERTIFICATE OF CORRECTION

PATENT NO. : 5,466,452

DATED : November 14, 1995

INVENTOR(S) : WHITTLE

It is certified that error appears in the above-indentified patent and that said Letters Patent is hereby corrected as shown below:

Column 1, line 9, "symptomotology" should read --symptomatology--.

Column 1, line 13, before "of" delete the indentation.

Column 1, line 26, "have" should read --has--.

Column 1, line 39, "principle" should read --principal--.

Column 2, line 24, "principals" should read --principles--.

Column 3, line 14, "saccharomyces cerevisiae" should read --*Saccharomyces cerevisiae*--.

Column 3, line 21, "in" should read --*in*--.

Column 3, line 22, "situ" should read --*situ*--.

Column 4, line 19, "*augustifolia*" should read --*angustifolia*--.

Column 4, line 20, "Tribu-" should read --*Tribu*---.

Column 4, line 21, "lus terrestris" should read --*lus terrestris*--.

Column 4, in the table of Example 1, sixth entry "rub" should read --*rub.*--

UNITED STATES PATENT AND TRADEMARK OFFICE
CERTIFICATE OF CORRECTION

PATENT NO. : 5,466,452

DATED : November 14, 1995

INVENTOR(S) : WHITTLE

It is certified that error appears in the above-indentified patent and that said Letters Patent is hereby corrected as shown below:

Column 5, line 16, "days" should read --days'--.

Column 6, in the table of Example 4, fifth entry "rub." should read --*rub.*--

Column 6, line 19, "days" should read --days'--.

Column 6, in the table of Example 5, "*Radicis*" should read --*radicis*--.

Column 6, line 37, "quanitites" should read --quantities--.

Column 6, in the table of Example 6, "*Radicis*" should read --*radicis*--.

Column 6, line 59, "days" should read --days'--.

Column 7, line 28, "*Palmatum*" should read --*palmatum*--.

Column 7, in the table of Example 10, ">0.2%" should read -->0.2%*--.

Column 8, line 6, "is" should read --are-- and "Example 11" should be centered as a title on the next line.

Column 8, line 14, "*Tribuli*" should read --*tribuli*--.

Column 8, line 15, "Lacca" should read --*Lacca*--.

Column 8, line 28, "bakers" should read --baker's--.

UNITED STATES PATENT AND TRADEMARK OFFICE
CERTIFICATE OF CORRECTION

PATENT NO. : 5,466,452

DATED : November 14, 1995

INVENTOR(S) : WHITTLE

Page 3 of 4

It is certified that error appears in the above-indentified patent and that said Letters Patent is hereby corrected as shown below:

Column 8, line 44, "consistancy" should read --consistency--.

Column 8, line 53, "days" should read --days'--.

Columns 9 and 10 (TABLE I-continued):

Column 2, row 2, "augustifolia" should read --*angustifolia*--.
    Column 5, row 2, "pityriasi8" should read --pityriasis--.
    Column 5, row 4, "pnnitus" should read --pruritus--.
    Column 2, row 6, "Lopatheri" should read --*Lophatheri*--.
    Column 4, row 7, "aniitubercular" should read --antitubercular--.
    Column 5, row 8, "oedemia" should read --oedemtia--.
    Column 5, row 8, "prelapse" should read --prolapsed--.

Column 11 and 12 (TABLE I-continued)

Column 5, row 2, "anaemic" should read --anaemia--.
    Column 5, row 5, "leukorrhea" should read --leukorrhoea--.
    Column 5, row 5, "lymphedema" should read --lymphoedema--.
    Column 2, row 6, "Rh" should read --*Rh.*--.
    Column 3, row 6, "Lactones" should read --lactones--.
    Column 4, row 6, after "coronary" insert --vaso-- and after "peripheral" insert --vaso--.
    Column 5, row 7, "Angina, pectoris" should read --Angina pectoris--.
    Column 4, row 13, "Anti-micobial" should read --Anti-microbial--.
    Column 4, row 14, "Hypotensive muscle" should read --Hypotensive, muscle--.

UNITED STATES PATENT AND TRADEMARK OFFICE
CERTIFICATE OF CORRECTION

PATENT NO. : 5,466,452

DATED : November 14, 1995

INVENTOR(S) : WHITTLE

It is certified that error appears in the above-indentified patent and that said Letters Patent is hereby corrected as shown below:

Column 11, line 61, "used define" should read --used to define--.

Column 12, line 64, "*Cortex radicis*" should read --Cortex radicis--.

Column 13, line 10, "pruritis" should read --pruritus--.

Column 13, line 38, "*augustifolia*" should read --*angustifolia*--.

Column 14, line 57, "*augustifolia*" should read --*angustifolia*--.

Column 14, line 63, "comprise" should read --comprises--.

Signed and Sealed this

Twenty-eighth Day of October, 1997

Attest:

BRUCE LEHMAN

Attesting Officer

Commissioner of Patents and Trademarks